(12) United States Patent
Koh et al.

(10) Patent No.: US 11,222,723 B2
(45) Date of Patent: Jan. 11, 2022

(54) METHOD AND SYSTEM FOR COUNTING AND IDENTIFYING VARIETY OF DEVICES

(71) Applicant: A Plus International Inc., Chino, CA (US)

(72) Inventors: Edward V Koh, Diamond Bar, CA (US); William M Adams, Coto De Caza, CA (US); Wayne W Lin, Diamond Bar, CA (US)

(73) Assignee: A Plus International Inc., Chino, CA (US)

( * ) Notice: Subject to any disclaimer, the term of this patent is extended or adjusted under 35 U.S.C. 154(b) by 0 days.

(21) Appl. No.: 16/564,399

(22) Filed: Sep. 9, 2019

(65) Prior Publication Data

US 2020/0402653 A1 Dec. 24, 2020

Related U.S. Application Data

(63) Continuation-in-part of application No. 16/447,959, filed on Jun. 21, 2019, now abandoned.

(51) Int. Cl.
| | |
|---|---|
| *G16H 40/40* | (2018.01) |
| *G06K 19/08* | (2006.01) |
| *G06K 19/077* | (2006.01) |
| *G06K 19/02* | (2006.01) |
| *G06K 19/06* | (2006.01) |

(52) U.S. Cl.
CPC ........... *G16H 40/40* (2018.01); *G06K 19/022* (2013.01); *G06K 19/06037* (2013.01); *G06K 19/0776* (2013.01); *G06K 19/07775* (2013.01); *G06K 19/083* (2013.01)

(58) Field of Classification Search
CPC ...... G16H 40/40; G16H 40/60; G06K 19/022; G06K 19/06037; G06K 19/0776; G06K 19/07775; G06K 19/083; A61M 2039/0045; A61M 25/0012; A61B 2090/3966
See application file for complete search history.

(56) References Cited

U.S. PATENT DOCUMENTS

| | | | | |
|---|---|---|---|---|
| 6,083,163 | A * | 7/2000 | Wegner | B25J 9/1679 600/429 |
| 2007/0125392 | A1* | 6/2007 | Olson | A61B 90/98 128/899 |
| 2008/0147529 | A1* | 6/2008 | Kreiner | H04W 4/02 705/34 |

(Continued)

*Primary Examiner* — Thien M Le
*Assistant Examiner* — Asifa Habib
(74) *Attorney, Agent, or Firm* — Jen-Feng Lee, Esq.

(57) ABSTRACT

The invention relates to a method and system that uses ultra-high frequency (UHF) radio frequency identification (RFID) for counting and identifying a variety of objects during medical or surgical operations. The method includes passive UHF RFID tag, a RFID scanner to communicate with host equipment and storage in a database cloud. The method includes a water-proof antenna and microchip supported by a substrate with covering overlay materials. The invention further discloses a tracking method for counting process, with software implementation, to assist the count-in count-out function to track multiple medical devices, resulting in reduction of counting errors during surgical procedures when the current UHF RFID process is utilized.

1 Claim, 14 Drawing Sheets

(56) References Cited

U.S. PATENT DOCUMENTS

| | | | |
|---|---|---|---|
| 2013/0154809 A1* | 6/2013 | Subramanian | G06K 7/0008 340/10.42 |
| 2014/0194733 A1* | 7/2014 | Goforth | A61K 49/0414 600/424 |
| 2015/0018671 A1* | 1/2015 | Marentis | A61B 6/12 600/424 |
| 2016/0210548 A1* | 7/2016 | Blair | G06K 19/0723 |
| 2018/0344429 A1* | 12/2018 | Stewart | A61B 90/90 |
| 2018/0353256 A1* | 12/2018 | Stewart | G16H 40/20 |
| 2019/0000589 A1* | 1/2019 | Vanderwoude | A61F 13/551 |
| 2019/0074574 A1* | 3/2019 | Augustine | H01Q 7/00 |
| 2019/0304598 A1* | 10/2019 | Hansen | A61B 46/00 |

* cited by examiner

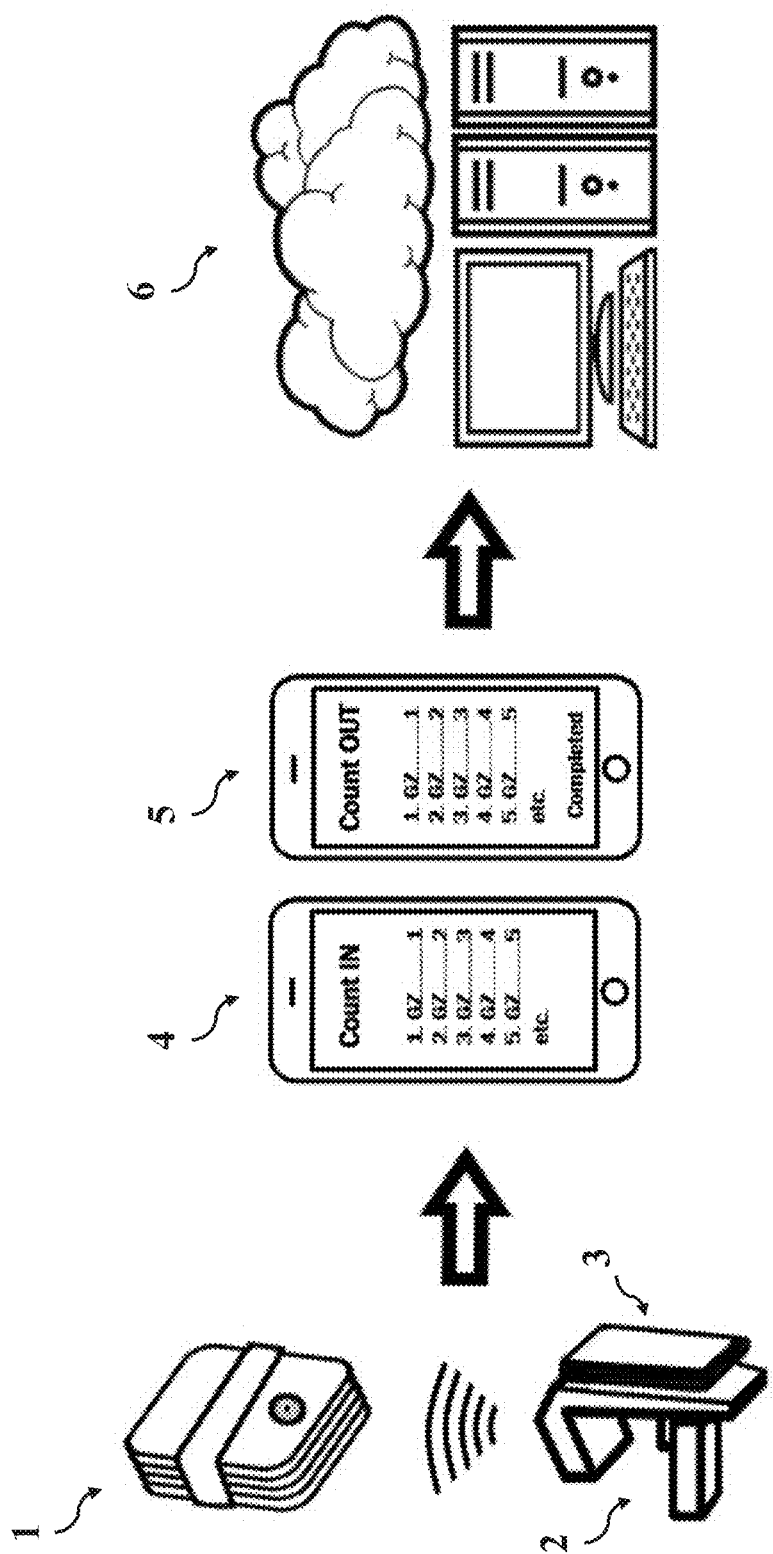

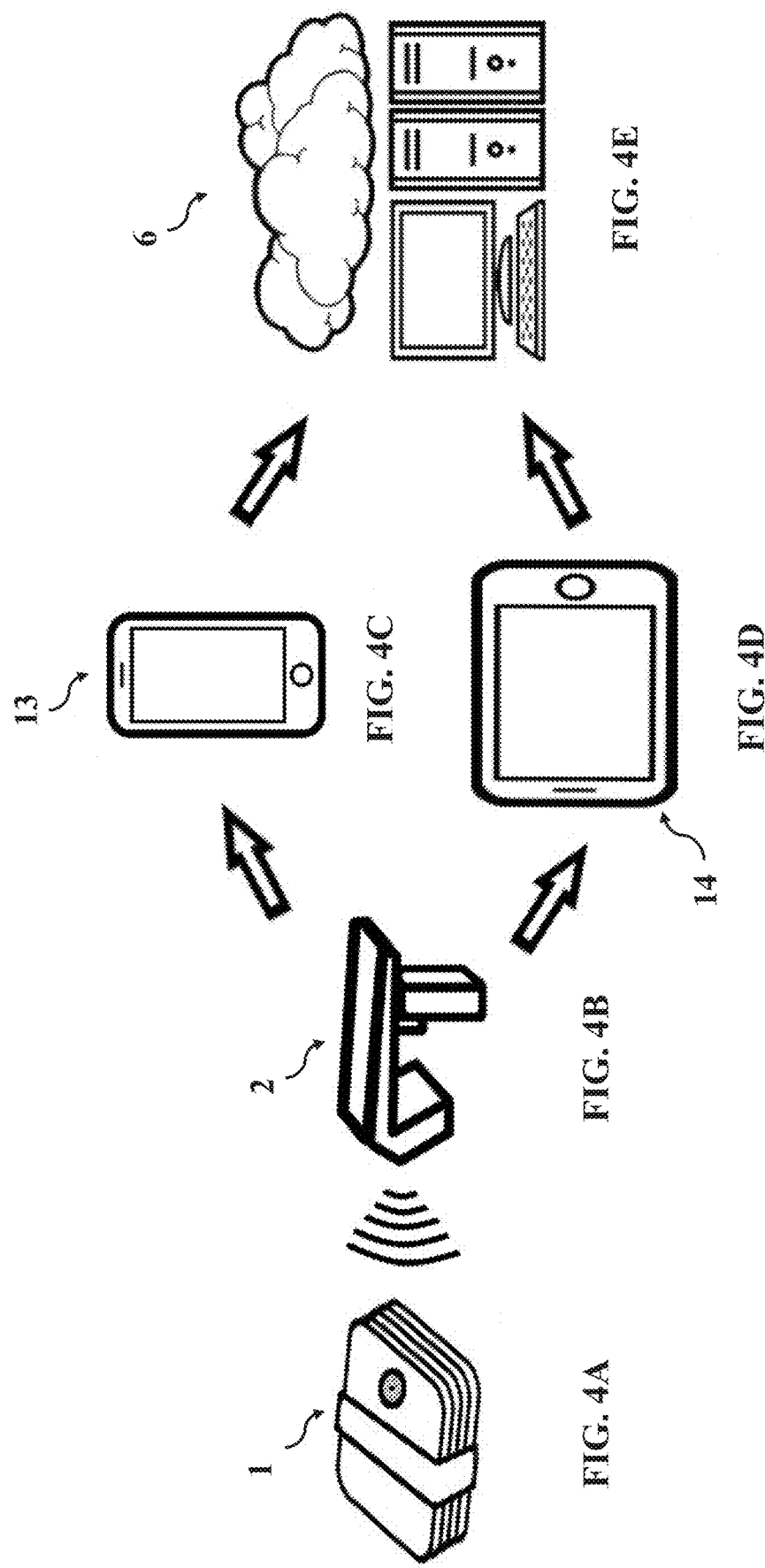

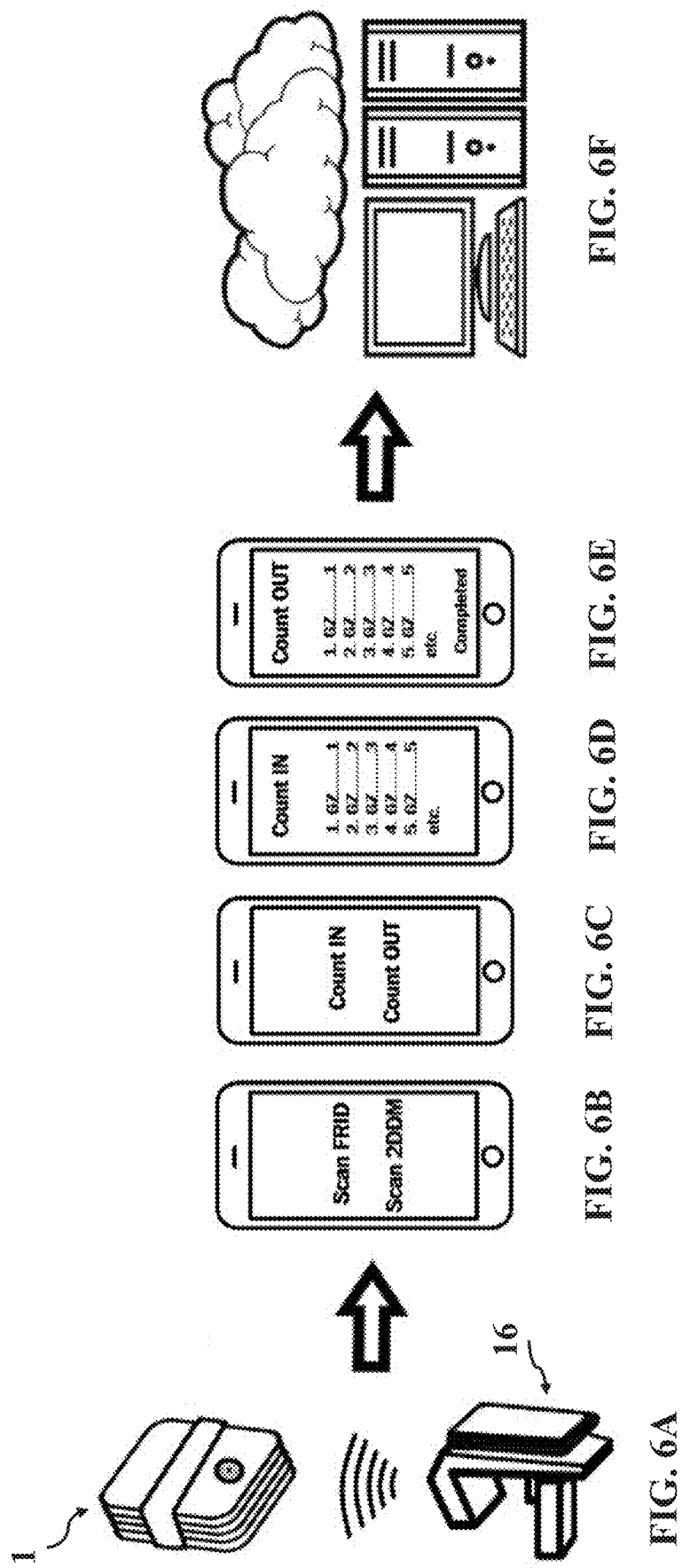

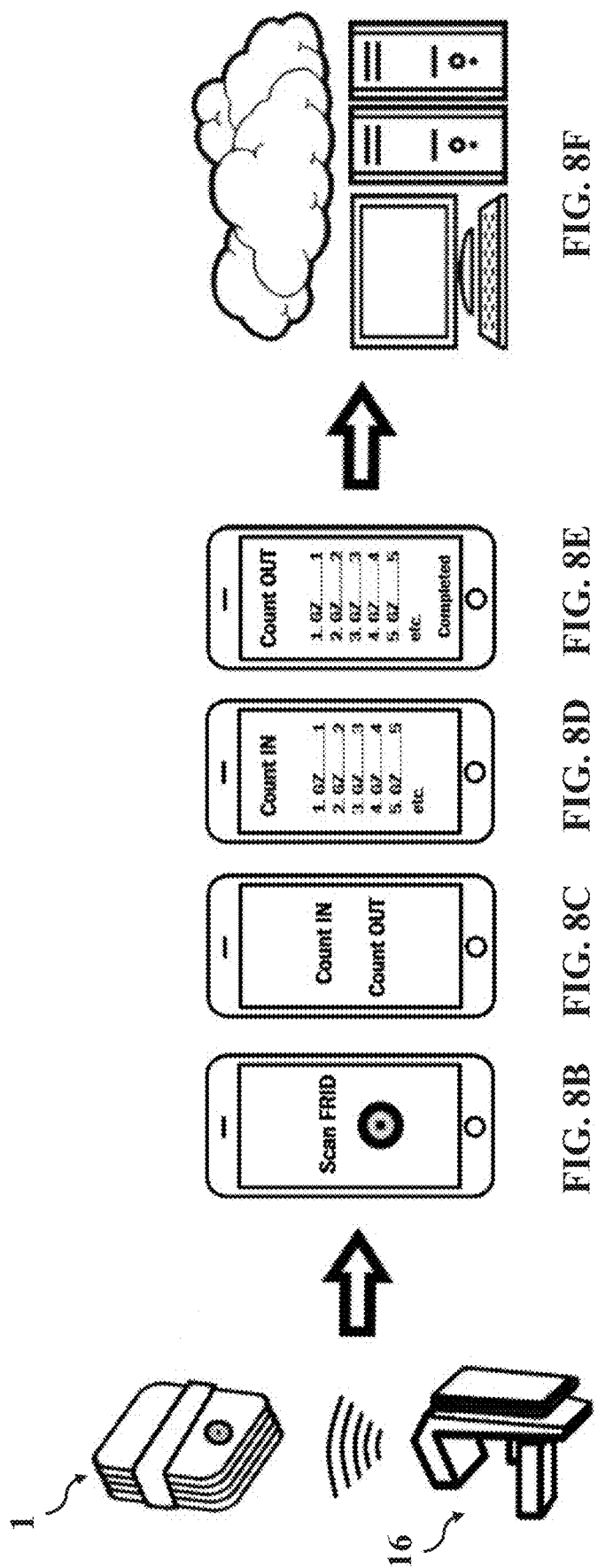

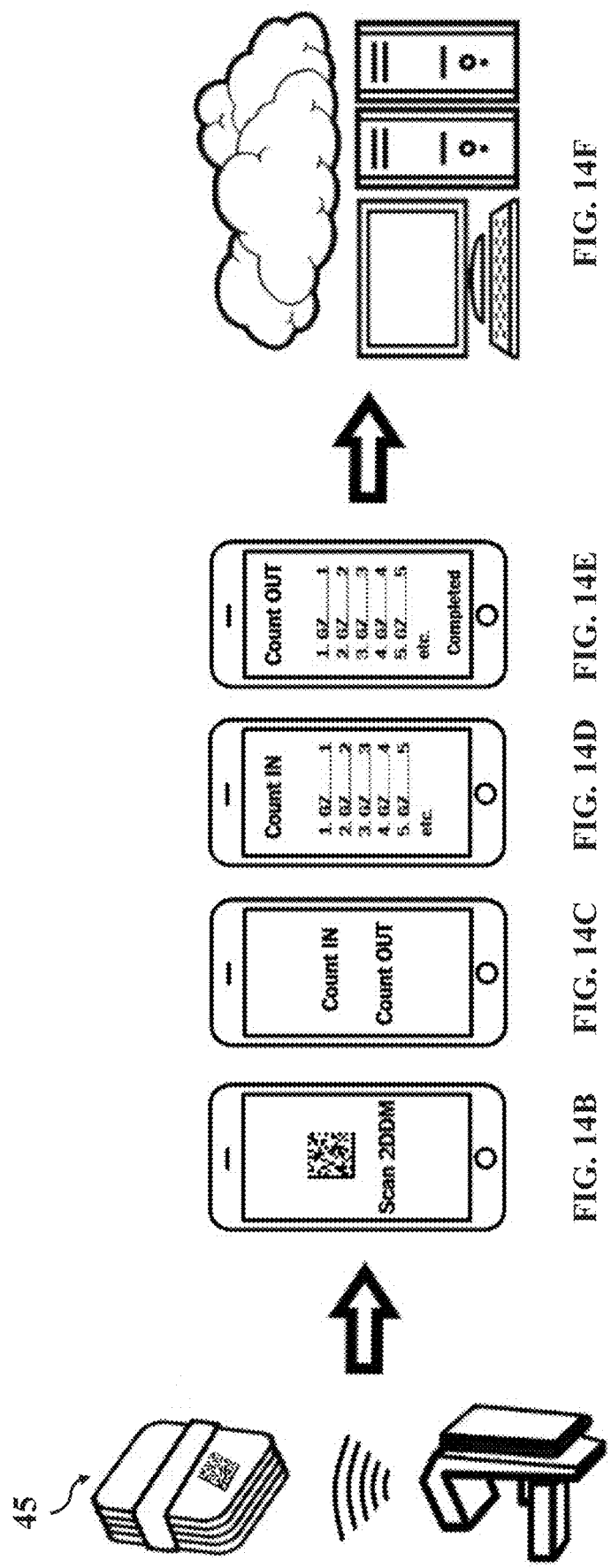

METHOD AND SYSTEM FOR COUNTING AND IDENTIFYING VARIETY OF DEVICES

CROSS REFERENCE TO RELATED APPLICATIONS

This application claims the benefit of U.S. application Ser. No. 16/447,959, filed on Jun. 21, 2019, which in turn claimed the benefit of U.S. Provisional Patent Application No. 62/688,026, filed Jun. 21, 2018, which is hereby incorporated by reference in its entirety.

FIELD AND BACKGROUND OF THE INVENTION

Field of the Invention

The present invention relates to a tag device, a system and a method of counting and identifying medical devices or surgical articles, for example gauze sponges, lap sponges, and/or O.R. towels, which are tagged with UHF RFID for surgical operations.

BACKGROUND OF THE INVENTION

Radio-frequency identification (RFID) methods are widely used in many applications, including inventory management system, security system, smart cards, item tracking in manufacturing, selling goods in retail, etc. A RFID scanner or reader can be configured to read the memory of RFID tag attached to objects.

During surgical operations, medical devices such as gauze sponges, lap sponges, and/or O.R. towels are used inside patients during surgery to absorb fluids, wall off organs and help create a good operative site. Surgical sponges come in different sizes for use in different areas in a patient. After absorbing blood and other body fluids in and around the incision site, they may become camouflaged in the body and can be extremely difficult to identify and may become retained inadvertently in the patient.

Retained Surgical Sponges (RSS) are defined by the Joint Commission as the number 1 surgical "Never Event". A Never Event is described as something that should "never" happen to a patient while in the care of a healthcare provider. Unfortunately, RSS still are occurring approximately thousands of times per year based on millions of medical procedures every year. The event can cause patients illness, mortality, temporary injuries, or permanent injuries. Patients can remain asymptomatic for up to several years compounding the problem significantly. The other issue is the patient becomes a plaintiff in these cases and the nurse is generally the defendant as he/she is responsible for the surgical count. Settlements of compensations have been significantly increased plus additional large amount of punitive damages.

Since the risk of a surgical sponge being retained inside a patient presented great risk to the patient and challenges to healthcare providers, standard sponge counting protocol has been developed and required by hospital to follow policies. Surgical sponges, surgical instruments and surgical needles are all largely managed through a manual counting process performed by two nurses. The manual counting protocol required that surgical sponges are "counted in" and the number is recorded on a white board prior to surgery, then sponges are "counted out" once they are removed from the patient and the sterile area. In the event of an "unreconciled count" (i.e. a sponge is unaccounted for) the surgeon will explore the wound while the nurses will look in the OR suite and around the patient. If the sponge cannot be located a Radiologist is called for an X-ray examination. This requires time while the patient is under anesthesia and is only accurate portion of the time with the first X-ray. In general, use manually counting procedure might not be efficient or effective, and is time consuming still having potential errors and risks.

Some other approaches for scanning of RF tags, RFID tags, or data matrix labels can be utilized as a method to assist counting surgical sponges. However, these approaches might not provide identification of the counting object, or might not able to assist searching locations of missing objects. Thus, a new and more convenient application to count and identify medical devices for surgical procedures and also to assist detects presence and absence of medical devices would be helpful.

SUMMARY OF THE INVENTION

1. Design of UHF RFID Tags

The present invention provides a counting and tracking method, using specifically designed ultra-high frequency (UHF) radio frequency identification (RFID) for counting and identifying variety of objects that include disposable and reusable medical devices or instruments during medical or surgical operations. This medical tracking process includes a passive radio frequency identification UHF RFID tag, an RFID scanner for detecting the passive UHF RFID tags and to communicate with host equipment via wireless technology, and to store in the database or cloud.

Having a sponge that had an UHF RFID tag on it would facilitate two critical issues for the patient and surgical team. The first issue is "accurate counting" through technological assistance. Every sponge would have a unique identifier that would be specific to a surgical procedure and specific patient. The technology assisted count would be done in combination with a manual count and be used to confirm the manual count and provide documentation that all sponges were accounted for.

The second issue is the "sponge location" once a sponge is not accounted for. Again, the UHF RFID application would also have a "detection" component so a nurse could use a "wand" (i.e. a UHF RFID scanner) to find a sponge in the O.R. or around a patient. Finding a sponge "in a patient" may be beyond the technologies limits as once you are in the body things like BMI (Body Mass Index), EMI (Electro Magnetic Interference) and ICD's (Implantable Cardiac Devices) can complicate the ability for the reader to get the signal from the UHF RFID tagged sponge.

RFID relies on bi-directional, wireless, transmission between readers and tags. In passive RFID systems, the readers emit a signal that induces a current in the RFID tag to power the tag's transmitter. There is a potential risk of interference between RFID and other technologies in the surgical room environment when using of wireless transmission. The RFID technology is used where the consequences of interference with other systems and equipment are likely to be serious.

More importantly, unlike low or high frequency RFID systems work around water because the radio waves within these frequencies can penetrate liquids; water poses a major problem to RFID tracking if UHF tags are being used, because UHF radio waves are absorbed by water. There are large amount of biological fluids surrounding medical devices during the surgical procedures.

The interference most commonly experienced with RFID systems results from environmental factors, such as during surgical operations. In the past, some difficulties were experienced when RFID technology was used when objects were associated with liquids, as the media interfered with the activation of the tag so that tags failed to respond to readers. There will be lots of biological fluids surrounding medical devices that could contain a large amount of water that absorb RF energy at the radio frequency used by passive UHF RFID system. It may cause problems because energy that has been absorbed is unavailable for use by the tag, which will not receive enough energy and not able to reflect back a strong signal for RFID scanner to be detectable.

Recent developments in tag and antenna design might have reduced some problems, and also select passive systems where transmission only occurs at the time of reading have less risk of interference. However, to improve detection efficiency and performance by reducing interference during surgical procedures the medical devices with UHF RFID tags are surrounded with biological fluids, the present invention provides an UHF RFID tag assembly comprising a microchip, integrated circle connected to the microchip, antenna of conducting material, supported by a substrate, and overlay covering around the inlay, wherein the integrated circuit with microchip and antenna are supported by a substrate and covered around by a water-resistant or waterproof overlay. The present invention has a specifically design inlay to be laminated between sheets of plastic or polymer layers to form a water-resistant or waterproof UHF RFID tag for attaching onto medical devices. This invention is able to provide protection to sealed tags and enhance performance.

The present invention will encode unique identification into each UHF RFID chip and other associated product information such as the type of the article, production batch or lot information, product name, SKU, descriptions, and/or pictures if needed for reference. Depends upon the final application and type of UHF RFID tag been utilized, typically a tag carries no more than 2 kilobytes (KB) of data will be enough to store intended basic information about the unique identification of each individual article.

The present invention of specifically designed software on mobile device will general a list on user interface that could also show additional information about the article that information has been previously encoded into the UHF RFID chip accordingly. When required by users, information such as the type of the article, production batch or lot information, product name, SKU, descriptions, and/or pictures if needed for reference can be stored into the chip and to be shown by the specifically designed software for mobile devices by the present invention.

The UHF RFID tags have a memory chip installed that can carry kilobytes of data to store basic information, which includes manufacturing serial number as unique identification numbers to be utilized for counting application. The present invention, information such as product descriptions or specifications may also be customized and encoded into memory chips that may include but not limit to the type of medical devices, the material of using, size, and other information. For example, when scan a piece of gauze with a uniquely custom-encoded UHF RFID tag for this application, a pre-stored information of GZ4416 plus unique identification number will be shown on the user interface of linked mobile device. This result indicates a piece of 4 inches by 4 inches of 16 ply gauze sponges has been scanned, identified, and counted by using the present invention of counting process. Another similar example of LS1818 plus unique identification number will be shown on the user interface when a piece of 18 inches by 18 inches of lap sponges has been canned, identified, and counted by using the present invention of counting process.

The overlay of UHF RFID tag for the present invention comprises a blank sheet, or a printed barcode, or a printed identification number as human readable information on the surface of top layer. In the case of if a RFID tag been damaged during the surgical operations and unable to read by RFID scanner, the printed human readable information could help identify the unique tag for counting process to compensate the counting quantity after counted-out step.

On the other hand, if the sponge cannot be located a Radiologist is called for an X-ray examination. This requires time while the patient is under anesthesia and is only accurate portion of the time with the first X-ray. Adding additional X-ray detectable material to the substrate may be helpful for further enhancement of X-ray detectability when needed.

2. Method of Counting and Identifying for Manufacturing Process

Healthcare providers and global medical device suppliers have often experienced incorrect count problems. It would be important to start counting accurately from manufacturing first, with solid production record as evidenced by quality record as well. The tracking process starts from implementing at manufacturing stages of the counting process to assure that correct quantity of medical devices is accurately counted for every bundle or batch as defined by product specifications. For example, a bundle of ten pieces of surgical gauze sponges has been manually counted during the production. Manually counted multiple times often required to reduce potential risks. Manually counting is necessary during the production process; however, it is labor intensive and costly process for manufactures.

Although manufacturing and packaging errors are rare, it has human process factors. When surgical sponges are re-packaged by kits packer or distributors, they are counted by humans. People make mistakes of miscount for 9 or 11 gauze sponge packages for a 10 pieces bundle. Many nurses or scrub technicians have encountered these miscounted packs, which may cause potential liability issues for manufactures who may need to face challenges if retained sponges occur.

The present invention provides a counting method and tracking process, uses specifically designed UHF RFID for manufactures to assist counting and identifying a variety of objects that includes disposable and reusable medical devices or instrument during the production stage, to ensure the accuracy of proper counting of multiple pieces of medical devises, for example, 10 pieces as a bundle for surgical gauze sponges or 5 pieces as a bundle for lap sponges.

The present invention provides a method of controlling a manufacturing process associated with counting procedures for medical devices use a scanner, which is capable of reading optical bar-code or data-matrix scanner, and also as an UHF RFID reader for identifying and counting during manufacturing stage, by (i) attach UHF RFID tags to medical devices at manufacturing stage, (ii) assembling a bundle or batch of specific quantity of medical devices that included UHF RFID tags been attached, (iii) scan each bundle or batch of medical devices as counted-in process, (iv) identifying RFID tags, by the counting process, performing scan again as counted-out step and to ensure all individual pieces has been identified and matched with the original input of counted-in process, and (v) then these medical devices been verified are ready to release for medical applications.

The act of counting medical devices to store in the database cloud to identify UHF RFID tags is critical to this technology. Either scanning single or multiple pieces of medical devices, the scanned data will be stored to database to identify UHF RFID tags having its own unique RFID tag numbers that correlate to single or multiple medical devices as specified input for counted-in or scanned-in step, wherein the medical devices may be gauze sponges, lap sponges, or O.R. Towels.

The act of counting the finished goods of medical devices from production comprises will generate a notification indicative of the one or more medical devices being identified and counted-out or scanned-out correctly when the quantity of the one or more RFID tags match the original designated quantity when counted-in or scanned-in during the prior manufacturing stage.

The act of counting medical devices comprises: using custom-build algorithm to identify and match counted-in and counted-out process for each bundle of medical devices with UHF RFID tags.

The act of counting medical devices further involves creating a list of counted-in items and counted-out items with their identification stored in mobile devices, and then using custom-build algorism to compare and match items from counting process.

The interface software shall identify and match counted-in and counted-out process for each bundle of medical devices with UHF RFID tags. In additional to show the identification number of each individual UHF RFID tag, the software is also capable of showing product name, SKU, descriptions, and/or pictures if needed for reference.

Due to the potential limitation for readability of RFID, when one tag is directly in the path of the subsequently tag, there might be a shadowing effect occurred that the following tag falls in the shadow of the previous tag thus not being detected or accounted for. This may affect the accuracy of counting process when multiple RFID tags are presented in a batch of multiple sponges. When preparing a bundle of medical devices, for example a bundle of 10 pieces of surgical gauzes sponges which are straightly lined up one gauze sponge behind another gauze sponge, to reduce the potential interference of shadowing effect, to position custom-build UHF RFID tag from present invention at proper position on the edge of sponges for better detection by scanner from the sideway of the bundle will help overcome the problems to ensure all UHF RFID tags within the bundle are capable of capture energy from reader respectfully.

Using a custom-built shielding box for production benches may also help reduce interference between multiple readers with appropriate reading angle to the UHF RFID tags, to help reduce the potential of RFID tag collision. Unlike surgical operations, which all sponges in the targeted surgical area need to be scanned for counting purpose to ensure all devices have been counted, there are potential interferences to readability of counting 15 accuracy during the manufacturing process of mass production when there are many bundles of surgical devices with multiple tags in process. A custom-built shielding cage to block RF emission waves helps eliminate unwanted interferences during the counting step. Using commercially available block material, such as combination of copper, nickel, polyester, or aluminum is utilized to build the shielding cage. During the counting step at manufacturing 20 process, the specific scanner and targeted bundle of surgical devices to be counted-in and counted-out will be performed inside the shielding cage to prevent potential unwanted interference from the surrounding mass production environment.

This invention provides accurately counted and absolutely correct quantities of medical devices as requested to healthcare users would be one the most important tasks for manufactures as great starting point for defending challenges from counting issues. Utilizing UHF RFID technologies tagged with medical devices not only provides an accurate counting method, but also provides solid production batch records as evidence of a quality document for manufacturing traceability.

3. Process of Counting and Identifying for Surgical Operations

Traditionally, sponge counting uses a wall-mounted dry erase board in surgical OR, and also use of plastic hanging Surgical Sponge Counter Bag mounted on a rack on an IV pole that help organizes the counting process in the OR. The surgical counts are entered on the dry-erase boards as record, which indicates a running total to see how many sponges are out.

The single most important element in the use of the hanging sponge counter bag and a sponge counting process is to make sure that the final count is taken; all the sponges that have been opened during the surgical case have been placed in the counter bags that all sponges have been accounted for, and none remain in the patient. This final step of surgical sponge verification is part of the debriefing in the surgical checklist. The expected outcome is zero cases of retained sponges. However, manually counting alone is insufficient. Every individual nurse is sure that their count is correct, yet there are retained sponges happened. Healthcare providers realize need for a better and reliable system because miscount incidents can happen with risks.

The present invention provides a counting and tracking process using specifically designed UHF RFID for nurses to assist counting and identifying variety of objects that includes disposable and reusable medical devices or instrument during surgical operations, to ensure the accuracy of proper counting of multiple pieces of medical devises. For example, 10 pieces of surgical sponges as a bundle or 5 pieces of lap sponges as a bundle. In additional to the traditional manual counting method and use of hanging sponge counter bag, the invention of providing a counting and identifying process for the surgical sponges with UHF RFID tag attached are designated for using in medical or surgical operation procedures.

The present invention of tracking process is thereby able to provide a counting record to enhance the quality by reducing counting errors. The RFID counting software provides quality record to be stored at database cloud indicating the presence of multiple medical devices with activated passive UHF RFID tag has been counted-in and counted-out during surgical procedures. This counting process helps confirm the manual count through the UHF RFID technology and locate a missing sponge outside the body that would be a significant improvement over most current practices in surgical operations.

The present invention comprises a process for facilitating counting of surgical sponges during the operations. Prior to surgery, the first step is to scan bundle of gauze sponges, lap sponges, and towels associated with UHF RFID tags as counting-in by using RFID scanner to scan all pieces. The customized user interface in a scanner linked mobile device shows a list of all medical devices that have been scanned, identified and counted-in for the designated surgical operation. By following the standard protocol, all surgical sponges will be placed to the counter bags accordingly during and after the surgical operation as usual. The next step after the surgical operation is to scan all those medical devices been used for the second time for counting-out. This invention provides a process that includes RFID scanner and associated interface and software, to perform final varication of scanning all surgical sponges in the counter bags all at once and simultaneously, as a counted-out step. The software will identify each individual piece and to verify that every counted-out sponge after the operation matches every counted-in sponge before the operation. Visually check the counted-out list from the customized user interface on the mobile device to verify that medical devices been used for the surgical operation have been completely recovered, identified, and counted-out. The user interface shows the counting process for targeted surgical operation has been completed.

In the case of a medical device is missing after counted-out process, the UHF RFID scanner with customized application can be utilized to assist finding the location or identifying of missing object with UHF RFID tag attached; additionally, assisting with visual and audio indicators. Because each article has unique identification of UHF RFID tag, the missing article or miss-counted article will be highlighted in the list of counted-out.

UHF RFID tags been utilized for this invention are passive tags, which do not contain battery, as they take power from RFID scanner or reader. Passive UHF RFID tags wait for a signal from an UHF RFID reader or scanner. The scanner sends energy to an antenna which converts that energy into an RF wave that is sent into the read-zone.

Select the specific missing article from the list of counted-out to be searching at "Find Tag" mode in the customized user interface, wherein the missing article will be selected and highlighted. Use a linked UHF RFID scanner to find the targeted missing article by sweeping the area of surgical operation. Once the missing article with UHF RFID tag is read within the read-zone, the RFID tag's internal antenna draws in energy from the RF waves and respond back to the RFID reader or scanner. This step is to utilize the specifically designed program for this invention to provide a responsive, audible, signal-strength, and a dynamic graphical signal to show the searching result of missing medical device with UHF RFID tag by rapidly scanning large areas and specifically locked into the missing article been searched only.

Check the intensity of the audio and graphic signal in the customized user interface to be increased when the missing article been detected during the search process to find the missing article with UHF RFID tag. When the scanner is getting closer to the missing article, the higher the intensity of audio and graphic signal will be shown. Once the missing article has been found, identified, and matched, the count-out process is completed and shown on the user interface on mobile device.

This invention provides counting process to accurately count and identify medical devices for healthcare providers to utilize a transparent, verifiable, standardized process to ensure "the counts are correct". Utilizing UHF RFID technologies tagged with medical devices not only provides an accurate counting process, but also provides solid scanned results and matched record will be stored at database cloud as evidence of quality record for traceability and eliminate liability to further prove there is nothing left behind.

Furthermore, the custom-build software for scanner linked with mobile device in present invention can block out all unintended or other untargeted RFID tags in complicated surgical environments, thus only focused on the specifically targeted surgical devices with unique custom-build UHF RFID tags. This will help simplify the counting process to count-in and count-out targeted surgical items only. Any other unwanted interference of RFID can be screened and blocked out that will not be shown on the user interface.

4. Process of Counting and Identifying by Using Two-Dimensional Data Matrix Barcodes for Manufacturing Process and Surgical Operations Two-dimensional data matrix (2DDM) barcodes could hold lots of data because they store information horizontally and vertically, which offers more storage capacity than standard linear barcodes. The 2DDM barcode system have been utilized for inventory management in warehousing, logistics, manufacturing and healthcare. The data matrix codes are two dimensional symbols laid out in square or rectangular grids that data is encoded horizontally and vertically in a series of dark and light blocks.

For the purpose of counting surgical sponges, customized information will be pre-printed on each 2DDM barcode label to provide unique identification for each label that will be attached to the surface of each surgical device. By using 2DDM barcode scanner, each device with unique 2DDM tag can be scanned as count-in and count-out process as a counting process for manufacturing process and surgical operations. This invention demonstrated that an embodiment of using the same unit of scanner with linked mobile device for scanning 2DDM to show the complete method to enable count-in and count-out process for various surgical devices. Alternatively, the same unit of handheld scanner also has the function for scanning liner barcode or two-dimensional data matrix tags by selecting desired function for scanning either RFID or 2D data matrix from custom-build user interface on linked mobile device.

The 2DDM barcode label includes heat sensitive adhesive, such as polyurethane based resin, that has been applied on the surface of the backside of the labels. This polymer-based adhesive could be heat-activated by using heat press machine to permanent bond 2DDM barcode labels to the surface of sponge or surgical devices. The same type of semi-automatic heat presses machine for attaching UHF RFID tags to surgical devices will also be using for attaching 2DDM barcode label to the surface of surgical devices, such as gauze, lap sponges, and towels. The pre-printed 2DDM barcode label with heat sensitive adhesive on the lower surface layer will be put onto the surface of surgical devices, and then the device with 2DDM barcode label will be loaded onto the lower platen and shuttled under the top heat platen of the heat press machine. The top flat platen will apply heat and pressure to the substrate by the upper-heating element. The hot platen is then pressed onto the device with 2DDM label for a specified duration which applies the necessary heat and pressure. When the adhesive has been applied to an elevated temperature, around 200° F. to 350° F. with pressure of 50 to 100 PSI for less than 10 seconds, the 2DDM barcode label will be held to the surface of the sponge or surgical device. Once cool down to lower temperature such as room temperature, the 2DDM barcode label will be permanent bonded to the surface of device with good bonding strength. Those surgical devices including 2DDM labels on the surface are now ready for 2DDM technologic assisted counting process.

Depends upon the type of surgical devices been selected for using this technologic assisted counting process, two different options for using UHF RFID or 2DDM can be selected individually for its associated counting process by using the same equipment set in present invention, included a specifically designed software with linked mobile device that can be utilized for UHF RFID application or 2DDM application. Similar to present invention of counting and identifying medical devices or surgical articles that were tagged with UHF RFID labels, the selected scanner and mobile device with associated application of custom-build software will be suitable for both UHF RFID and 2DDM barcode methods. By selecting the scanning option for either UHF RFID or 2DDM barcode application for the specifically customized option in user interface, the scanner will be switched to the selecting method, either for UHF RFID or 2DDM barcode application to scan articles with UHF RFID tags or 2DDM labels for counting process.

When 2DDM barcode method been selected in the user interface for counting process, the scanner will be performed as 2DDM barcode reader and communicate with a host mobile device via Bluetooth wireless technology. This reader can be switched scanning mechanism accordingly to be configured for scanning of 2DDM barcode data and connected to the same Bluetooth linked mobile device using Operating System including Android and iOS. The mobile device could be a smartphone, tablet, or other handheld device. The customized user interface software for associated mobile device will collect scanning data from 2DDM barcodes, to perform count-in and count-out process, and then store counting data into database or cloud as evidence of quality record.

During manufacturing process for surgical devices, when the 2DDM counting method to be selected, using the same handheld scanner with a linked mobile device for scanning articles having 2DDM labels, the application of custom-build user interface will be utilized to enable count-in and count-out process for various articles that have 2DDM barcode labels attached. This counting process for articles with 2DDM labels can be utilized during manufacturing process to validate the number of pieces for each bundle of articles have been confirmed and matched with intended quantities. For example, a bundle of 5 pieces of sponges can be count-in and record as five pieces by scanning each 2DDM on sponges, and then to be scanned second time as count-out to verify and confirm the quantity of 5 pieces of sponges were in this bundle when manufacturing. Unlike manually hand count quantity of sponges for each bundle, this 2DMM technology assisted counting process can provide solid counting record to be stored in the database with unique identification by scanning 2DDM labels on each sponge. In addition, this 2DDM counting process also to be considered as a simulation to the counting process at surgical operation.

For end users before perform surgical procedure at operation room and during the preparation, nurses or medical staffs will manually activate scanner with linked mobile device to start count-in process by click the 2DDM option and let scanner facing the 2DDM barcode label of targeted surgical articles with unique identification. Once "Scan 2DDM" option has been selected in the user interface software, the counting process will start by selecting count-in first. After the 2DDM tag has been scanned for intended surgical procedure, the user interface on mobile device will show a list of targeted articles that have been scanned, detected, and to be shown as counted-in. For example, a bundle of five pieces surgical sponges been counted-in, a list of unique identified article to show those 5 surgical sponges as count-in on the screen of mobile device. After surgical operation, the similar counting process to each 2DDM labels on each sponge will be scanned by using scanner as count-out step. Since each 2DDM label has its unique identification, the result of count-out step will not only to be matched with the quantity of count-in, but also need to be matched the unique identification of each 2DDM label from count-in. Once the counting result, both quantities and identifications from count-out matched the result from count-in, the user interface will show the counting process has been matched and completed. The result of counting and identifying process by using 2DDM method will then be stored into the database or cloud. The counting result will indicate and prove that all pieces of sponges have been successfully removed from targeted surgical operation and no piece was left behind the surgical operation.

The present invention provides accurately counted and absolutely correct quantities of surgical devices as requested to healthcare users would be one the most important tasks for manufactures as great starting point for defending challenges from potential counting issues. The present invention can utilize the same set of scanner with linked mobile device and customized software for both UHF RFID and 2DDM technologies for surgical devices, not only provides an accurate counting method, but also provides quality document of manufacturing production record and reliable technology assisted counting method with record for surgical procedure as solid evidence of quality record for traceability.

DESCRIPTION OF THE DRAWINGS

The accompanying drawings, which are incorporated in and constitute a part of this specification, illustrate and exemplify the preferred embodiments of the invention. Together with the description, serve to explain the principles of the invention. Further advantages of the invention are apparent by reference to the detailed description in conjunction with the figures, wherein elements are not to scale so as to more clearly show the details, wherein like reference numbers indicate like elements throughout the several views, and wherein:

A brief description of the drawings is as follows:

FIGS. 1A-1C show an exemplary of the counting process of the invention is demonstrated, a set of medical devices, scanner connected with mobile device, and secure storage of database.

FIGS. 4A-4E show a diagram showing an embodiment of a basic scanning process and method of the invention of using a scanner with mobile device, and to securely store counting record to database.

FIGS. 6A-6F illustrate an embodiment of the scanning process for two options of UHF RFID and 2DDM and method to enable count in and count out process for various sponges, and to securely store counting record to database.

FIGS. 8A-8F illustrate a flow of a process, respectively, of the invention of the scanning process for using an UHF RFID and method to enable count in and count out process for various sponges at manufacturing facilities, and to securely store counting record to database, such as product information, and unique identification for each sponge.

FIGS. 14A-14F illustrate an embodiment of using the same scanner linked mobile device for scanning 2DDM to show the complete method to enable count in and count out process for various sponges.

DETAILED DESCRIPTION OF THE PREFERRED EMBODIMENT

Figures 2A, 2B:
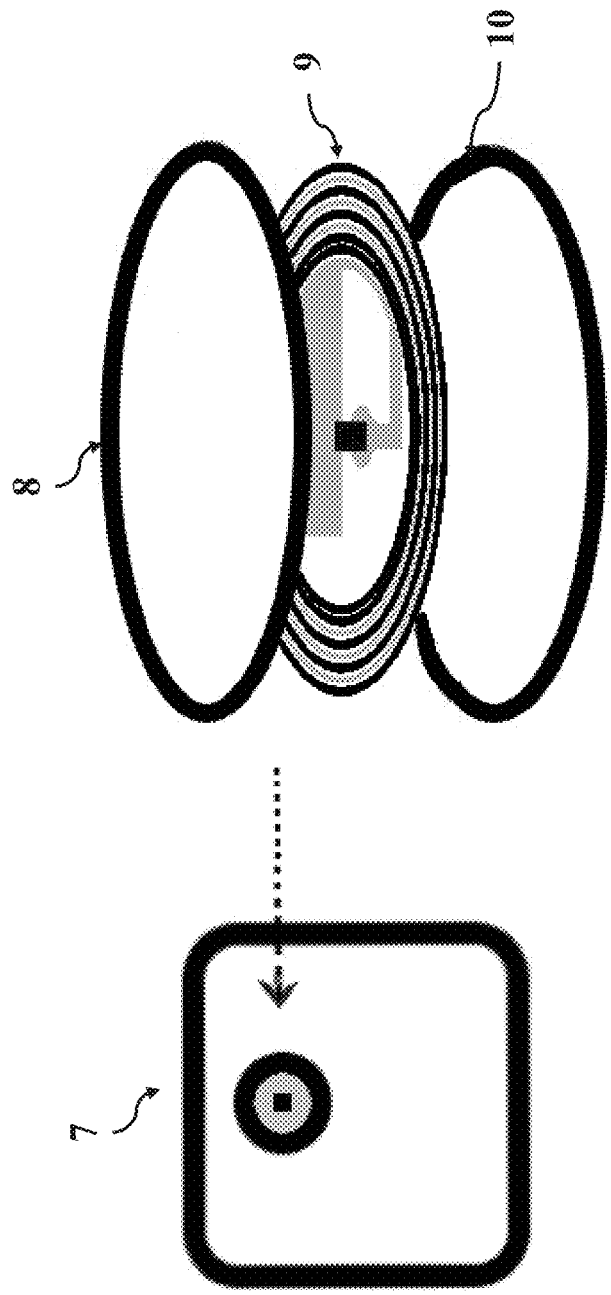
FIGS. 2A-2B show a design of water-resistant UHF RFID tag with embodiment of a chip-type micro electronic component, which is positioned in between polymer layers.

As shown in the figures, the present invention provides a counting method and tracking process, uses specifically designed ultra-high frequency radio frequency identification for counting and identifying variety of objects that includes disposable and reusable medical devices or instruments during medical or surgical operations. This medical tracking method includes a passive radio frequency identification UHF RFID tag, an RFID scanner for detecting the passive UHF RFID tags and to communicate with host equipment via wireless technology, and to store in the database or cloud.

FIGS. 1A-1C show an exemplary of the present invention for a technological assisted counting process is demonstrated, a set of disposable medical devices 1 as FIG. 1A, UHF RFID scanner 2 connected with mobile device 3 as FIG. 1B to demonstrate the user interface of count-in 4 and count-out 5 by using a specifically linked mobile device, and secure storage of database as FIG. 1C. All counting process for count-in and count-out would be stored into the computer using secure database 6 as quality record for both manufacture and hospitals.

The act of counting the finished goods of medical devices from production comprises will generate a notification indicative of the one or more medical devices being identified and counted-out or scanned-out correctly when the quantity of the one or more RFID tags match the original designated quantity when counted-in or scanned-in during the prior manufacturing stage. The interface software shall identify and match counted-in 4 and counted-out 5 process for each bundle of medical devices with UHF RFID tags. In additional to show the identification number of each individual UHF RFID tag, the software is also capable of showing product name, SKU, descriptions, and/or pictures if needed for reference.

The other unique aspect of present invention is the "find sponge location" once a sponge is not accounted for. The UHF RFID application would also have a "detection" component so a staff or nurse could use an UHF RFID scanner to find an article in the surgical area or around a patient.

1. Design of UHF RFID Tags

Unlike low or high frequency RFID systems work around water because the radio waves within these frequencies can penetrate liquids; water poses a major problem to RFID tracking if UHF tags are being used, because UHF radio waves are absorbed by aqueous such as water. There are large amount of biological fluids surrounding medical devices during the surgical procedures.

The interference most commonly experienced with RFID systems results from environmental factors, such as during surgical operations. In the past, some difficulties were experienced when RFID technology was used when objects were associated with liquids, as the media interfered with the activation of the tag so that tags failed to respond to readers. There will be lots of biological fluids surrounding medical devices that could contain a large amount of water that absorb RF energy at the radio frequency used by passive UHF RFID system. It may cause problems because energy that has been absorbed is unavailable for use by the tag, which will not receive enough energy and not able to reflect back a strong signal for RFID scanner to be detectable.

However, to improve detection efficiency and performance by reducing interference during surgical procedures the medical devices with UHF RFID tags are surrounded with biological fluids, the present invention provides an UHF RFID tag assembly comprising a microchip, integrated circle connected to the microchip, antenna of conducting material, supported by a substrate, and overlay covering around the inlay, wherein the integrated circuit with microchip and antenna are supported by a substrate and covered around by a water-resistant or waterproof overlay.

The antenna collects power from radio waves from a RFIP scanner and supplies the power to the IC. The antenna receives radio signals and also reflects back the received signals.

FIGS. 2A-2B show a design of water-resistant UHF RFID tag with embodiment of a chip-type micro electronic component, which is positioned in between water-resistant polymer layers. FIG. 2A shows an example of disposable medical devices article that includes an UHF RFID tag were securely attached to the surface of article 7. A specifically designed inlay to be laminated between sheets of RF translucent materials, such as plastic polymer 8-9, PE, or PVC layers, to form a water-resistant or waterproof UHF RFID tag as shown in FIG. 2B for attaching onto disposable medical devices. This invention is able to provide protection to sealed tags and enhance performance of detection when using UHF RFID system.

The inlay can be coated with adhesive to be attached to object devices such as gauze sponges, lap sponges, or O.R. Towels.

In order to keep UHF RFID tag securely attached to the surface of medical devices under the biological fluid environments, a thin layer of heat activated adhesive material is applied to the lower surface of the lower layer of the polymer 10 as shown in FIG. 2B. Adhesive to be activated at elevated temperatures with a combination of firm pressure and a few seconds dwell time. Depends upon the materials, optimum bonds can be achieved with various combinations of those three processing parameters. A set of experimentation for selecting these three parameters help determine the best process for the application of attaching UHF RFID tag to surgical sponge securely. The adhesive will be activated by applying pressure and heat to the UHF RFID tag when bonding the tag to the article. The duration of time to apply both pressure and heat will ensure the tag will be securely attached to the surface of article such as sponges.

The present invention will encode unique identification into each UHF RFID chip and other associated product information such as the type of the article, production batch or lot information, product name, SKU, descriptions, and/or pictures if needed for reference. Depends upon the final application and type of UHF RFID tag been utilized, typically a tag carries no more than 2 kilobytes (KB) of data will be enough to store intended basic information about the unique identification of each individual article as FIG. 2B. The information to be stored into UHF RFID chip will be encoded by RFID writer accordingly.

The UHF RFID tags have a memory chip installed that can carry kilobytes of data to store basic information, which includes manufacturing serial number as unique identification numbers to be utilized for counting application. The present invention, information such as product descriptions or specifications may also be customized and specially encoded into memory chips that may include but not limit to the type of medical devices, the material of using, size, and other information. For example, when scan a piece of gauze with a uniquely custom-coded UHF RFID tag for this application, a pre-stored information of GZ4416 plus unique identification number will be shown on the user interface of linked mobile device. This result indicates a piece of 4 inches by 4 inches of 16 ply gauze sponges has been scanned, identified, and counted by using the present invention of counting process. Another similar example of LS1818 plus unique identification number will be shown on the user interface when a piece of 18 inches by 18 inches of lap sponges has been canned, identified, and counted by using the present invention of counting process.

The overlay of UHF RFID tag for the present invention comprises a blank sheet, or a printed barcode, or a printed identification number as human readable information on the surface of top layer. In the case of if a RFID tag been damaged during the surgical operations and unable to read by RFID scanner, the printed human readable information could help identify the unique tag for counting process to compensate the counting quantity after counted-out step.

FIGS. 3A-3D are a diagram showing an embodiment of a heat press equipment to prepare and combine UHF RFID tag with sponge 11, and also to build a set of sponges as a bundle. Unlike other designs of UHF RFID tag for general applications, this specifically designed water-resistant UHF RFID tag of present invention will be placed on the top of disposable medical device of article such as gauze, sponges, or towel as FIG. 3A will be placed into the heat press equipment 12 as FIG. 3B. A semi-automatic heat presses machine will be using for this application. It has flat platen to apply heat and pressure to the substrate by the upper-heating element. The sponge with UHF RFID tag will be loaded onto the lower platen and shuttled under the top heat platen. The hot platen is then pressed onto the tag with sponge for a specified duration which applies the necessary heat and pressure. The UHF RFID tag includes heat activated adhesive, such as commercially available polyurethane-based resin, has been applied on the surface of the backside of the tags. This polymer-based adhesive could be heat-activated by using heat press machine to permanent bond UHF RFID tag to the surface of sponge. When the adhesive has been applied to an elevated temperature, around 200° F. to 350° F. with pressure of 50 to 100 PSI for less than 10 seconds, the UHF RFID tag will be held to the surface of the sponge. Once cool down to lower temperature such as room temperature, the UHF RFID tag will be permanent bonded to the surface of sponge with good bonding strength. Apply defined heat and pressure at certain duration will securely attached the tag onto the surface of article as FIG. 3C, as this will be the preferred method to attach tags. In addition, an alternative option would be using semi-automatic sewing machine to sew the UHR RFID tag onto the surface of the sponge devices. This sewing method is to carefully sew the tag area around the edges onto the fabric of sponges without damaging any portion of the antenna. Or, by inserting the UHF RFID tag into the second layer of sponges, as a thin layer of cotton fabric will be utilized to cover the UHF RFID to provide more surface area to cover the tag for sewing the inserted tag into the sponges. Thus, the UHF RFID tag will not be located on the top surface of the sponges, instead, the tag will be covered by one or few thin layers of fabrics in the sponges. The sewing option could be considering as an enhancement to attach tags to the surgical sponges if needed. Meanwhile, use heat-activated adhesive with heat-press machine at present invention is the preferred method for attaching both UHF RFID tag and 2DDM barcode labels to surgical sponges.

Due to the potential limitation for readability of RFID, when one tag is directly in the path of the subsequently tag, there might be a shadowing effect occurred that the following tag falls in the shadow of the previous tag thus not being detected or accounted for. This may affect the accuracy of counting process when multiple RFID tags are presented in a batch of multiple sponges. When preparing a bundle of medical devices, for example a bundle of 10 pieces of surgical gauzes sponges which are straightly lined up one gauze sponge behind another gauze sponge, to reduce the potential interference of shadowing effect, to position custom-build UHF RFID tag at proper position on the edge of sponges for better detection by scanner from the sideway of the bundle will help overcome the problems to ensure all UHF RFID tags within the bundle are capable of capture energy from reader respectfully.

Figure 3A:
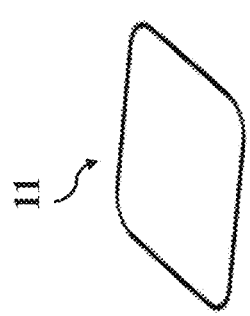
FIGS. 3A-3D are a diagram showing an embodiment of a heat press process to prepare and combine UHF RFID tag with sponge, and also to build a set of sponges as a bundle.
Figure 3B:
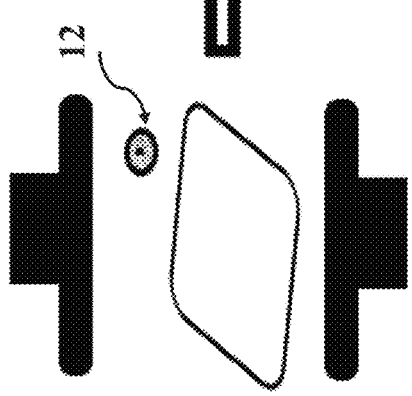
Figure 3C:
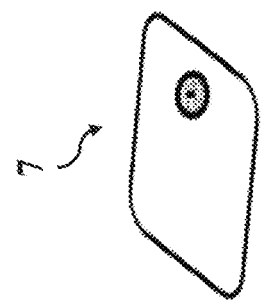
Figure 3D:
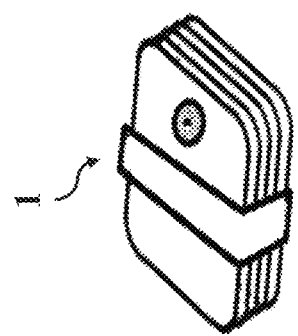

Depends on the specifically designed applications for the surgical operation or procedure kits, a specifically number of articles 7 will be bundle together by using paper band which has adhesive at one end to bond together as a loop to hold this bundle of articles 1 as FIG. 3D. Examples of those bundles are ten pieces of surgical gauzes that each gauze has its unique identification of UHF RFID tag as a bundle of ten pieces of articles. Five pieces of lap sponges that each lap sponge has its unique identification of UHF RFID tag as a bundle of five pieces of articles 1. Multiple pieces of towels that each towel has its unique identification of UHF RFID tag as a bundle for the application of surgical operations.

An additional X-ray detectable material is added to enhance the detectability of the UHF RFID tag The detectable filament material such as Barium Sulfate can be added, or incorporated into the substrate, especially in the situation where the sponge cannot be located easily and a Radiologist is called for an X-ray examination.

2. Method of Counting and Identifying for Manufacturing Process

The present invention provides a counting method and tracking process, uses specifically designed UHF RFID for manufactures to assist counting and identifying a variety of objects that includes disposable and reusable medical devices or instrument during the production stage, to ensure the accuracy of proper counting of multiple pieces of medical devises, for example, 10 pieces as a bundle for surgical gauze sponges or 5 pieces as a bundle for lap sponges.

FIGS. 4A-4E are a diagram showing an embodiment of a basic scanning process and method of the invention of using a scanner with a specific Bluetooth linked mobile device, and to securely store counting record to database. After assembling those specifically designed articles as bundles 1, a bundle of multiple articles 1 that each article includes its unique individual identification of UHF RFID tag as FIG. 4A will be scanned by a RFID scanner or handheld UHF RFID scanner 2 as FIG. 4B. A mobile device such as smart phone 13 as FIG. 4C or tablet 14 as FIG. 4D will be utilized at production line to scan those bundle as one bundle of articles at a time for both count-in and count-out of the present invention of counting process. Scanned data via a linked mobile device will be processed by computer and stored into the database 6 as FIG. 4E as a unique technological assisted method for counting articles as evidence of quality record.

Figure 5A:
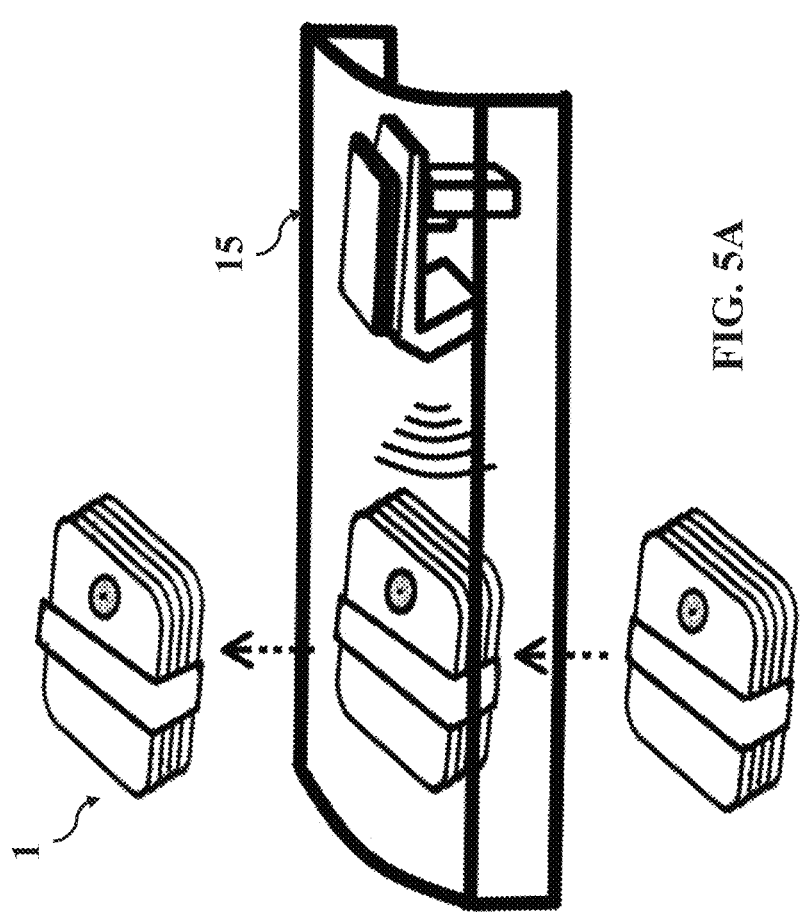
FIGS. 5A-5B illustrate an embodiment of a scanning process and manufacturing flow to enable detection of a bundle of sponges at manufacturing facilities, and to securely store counting record to database.
Figure 5B:
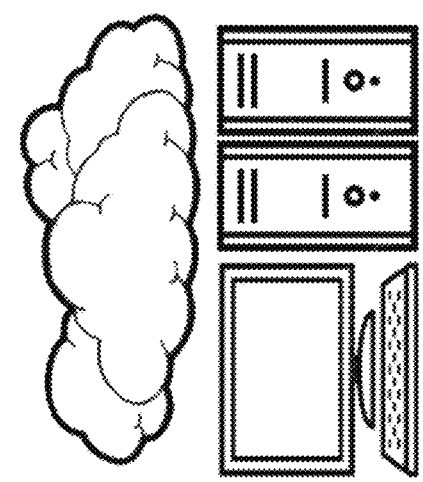

FIG. 5 illustrates an embodiment of a scanning process and manufacturing flow to enable detection of a bundle of sponges at manufacturing facilities, and to securely store counting record to database. Each bundle of multiple articles 1 that each article within includes its unique individual identification of UHF RFID tag as FIG. 5A will be scanned by a RFID scanner or handheld UHF RFID scanner one bundle at a time. Each bundle of articles will be first scanned as count-in and then the same bundle of articles will be scanned the second time as count-out to complete the counting process of the present invention of counting process. Scanned data via a linked mobile device will be processed by computer and stored into the database FIG. 5B as a unique technological assisted method for present invention of counting articles as evidence of quality record.

Although RFID system provide a technologic assisted counting process to help automatically counting articles, however, incorrect tracking of not intended articles could yield erroneous data, which defeats the purpose of a RFID tracking process. This is a critical issue for the production line when dealing with significant large number of articles to be scanned one bundle at a time. In particular, other bundles of articles in the neighborhood environment as FIG. 5A that are waiting to be scanned may be detected by the RFID scanner while perform the scanning process for specifically targeted bundle of articles for count-in and count-out step. The present invention designs a RFID shielding cage as 15 in FIG. 5A that will effectively record targeted bundle of articles with UHF RFID tags while excluding the signals of unwanted ones at crowded and busy production line.

When preparing a bundle of medical devices, for example a bundle of 10 pieces of surgical gauzes sponges which are straightly lined up one gauze sponge behind another gauze sponge, to reduce the potential interference, to position UHF RFID at proper position on sponges will help overcome the problems to ensure all UHF RFID tags within the bundle are capable of capture energy from reader respectfully. Using a custom-built shielding cage 15 as FIG. 5A for production benches may help reduce interference between multiple readers with appropriate reading angle to the UHF RFID tags, to help reduce the potential of RFID tag collision.

There are potential interferences to readability of counting accuracy during the manufacturing process of mass production when there are many bundles of surgical devices with multiple tags in process. A custom-built shielding cage to block RF emission waves helps eliminate unwanted interferences during the counting step. Use commercially available blocking material, such as combination of copper, nickel, polyester, or aluminum is utilized to build the shielding cage. The RFID shielding cage 15 in FIG. 5A utilize RFID absorbing material or shielding material by aluminum, or incorporated with copper and nickel material to build a cage that will protect and isolate the targeted bundle of articles and RFID scanner. Other near and around RFID transmit and receive antennas or handheld RFID scanner to will be blocked or shield to eliminate unwanted crosstalk and also to enhance signal integrity. During the counting step at manufacturing process, the specific scanner and targeted bundle of surgical devices to be counted-in and counted-out will be performed inside the shielding cage to prevent potential unwanted interference from the surrounding mass production environment. Custom-build copper mesh door with conductive gaskets also help this shielding cage to block RF emission from outside the cage, and prevent RF emission leaking out of the cage from specific scanner for targeted bundle of surgical devices during count-in and count-out process. Thus, each production line at mass production of manufacturing area will have a shield cage to isolate their own RFID scanner for scanning and collecting unique identification of specific bundle that is its targeted as FIG. 5A.

Once the targeted bundle of articles with UHF RFID has been counted successfully for both scan-in and scan-out process, the successful targeted bundle of article will then be removed from the shielding cage and more to the next step of the manufacturing stage. All counting information as count-in and count-out will be process by computer and store at database as FIG. 5B. The next bundle of articles in waiting at production line will be moved into the shielding cage as the next targeted bundle of articles to be ready for scanning by RFID scanner or reader. The present invention of shielding cage FIG. 5A can ensure only the targeted articles will be detected, identified, counted, and stored at database FIG. 5B, while the shielding cage helps prevent misreads of untargeted bundle of articles.

The present invention is to design a technologic assisted method of controlling a manufacturing process associated with counting procedures for medical devices use a scanner, which is capable of reading optical bar-code or two dimensional data-matrix (2DDM) scanner, and also as an UHF RFID reader for identifying and counting during manufacturing stage, by (i) attach UHF RFID tags to medical devices at manufacturing stage, (ii) assembling a plurality of medical devices that included UHF RFID tags been attached, (iii) scanning the plurality (each bundle or batch) of medical devices as counted-in process, (iv) identifying RFID tags, by performing scan again as counted-out step and to ensure all individual pieces has been identified and matched with the original input of counted-in process, and (v) then verifying the medical devices can be released for their intended medical applications.

FIGS. 6A-6F illustrate an embodiment of the scanning process 1 as FIG. 6A for two options of UHF RFID and 2DDM methods as FIG. 6B to enable count in and count out process for various sponges, and to securely store counting record to database process. Depends upon the type of articles been selected for using this technologic assisted counting process, two different options can be selected individually for its associated counting process. The present invention included a specifically designed software for the linked mobile device that can be utilized for UHF RFID application or 2DDM application as FIG. 6B. Once Scan RFID or Scan 2DDM option has been selected on FIG. 6B, the user interface software on linked mobile devise will show a selection for the counting process as FIG. 6C. The counting method will start by selecting count-in first at user interface in FIG. 6C. A activated RFID scanner with linked mobile device will start count-in process manually by click the RFID scanner facing a bundle of targeted articles with unique identification of UHF RFID tags.

The user interface on mobile device will show a list of targeted articles that been scanned, detected, and counted-in as FIG. 6D. An example of bundle of five pieces surgical sponges 1 been counted-in, a list of unique identified article to show those 5 surgical sponges as FIG. 6D. Each bundle of articles will be first scanned as count-in and then the same bundle of articles will be scanned the second time as count-out to complete the counting process of the present invention of counting process FIG. 6E. Scanned data via a linked mobile device will be processed by computer and stored into the database FIG. 6F as a unique technological assisted method for present invention of counting articles as evidence of quality record.

Figure 7:
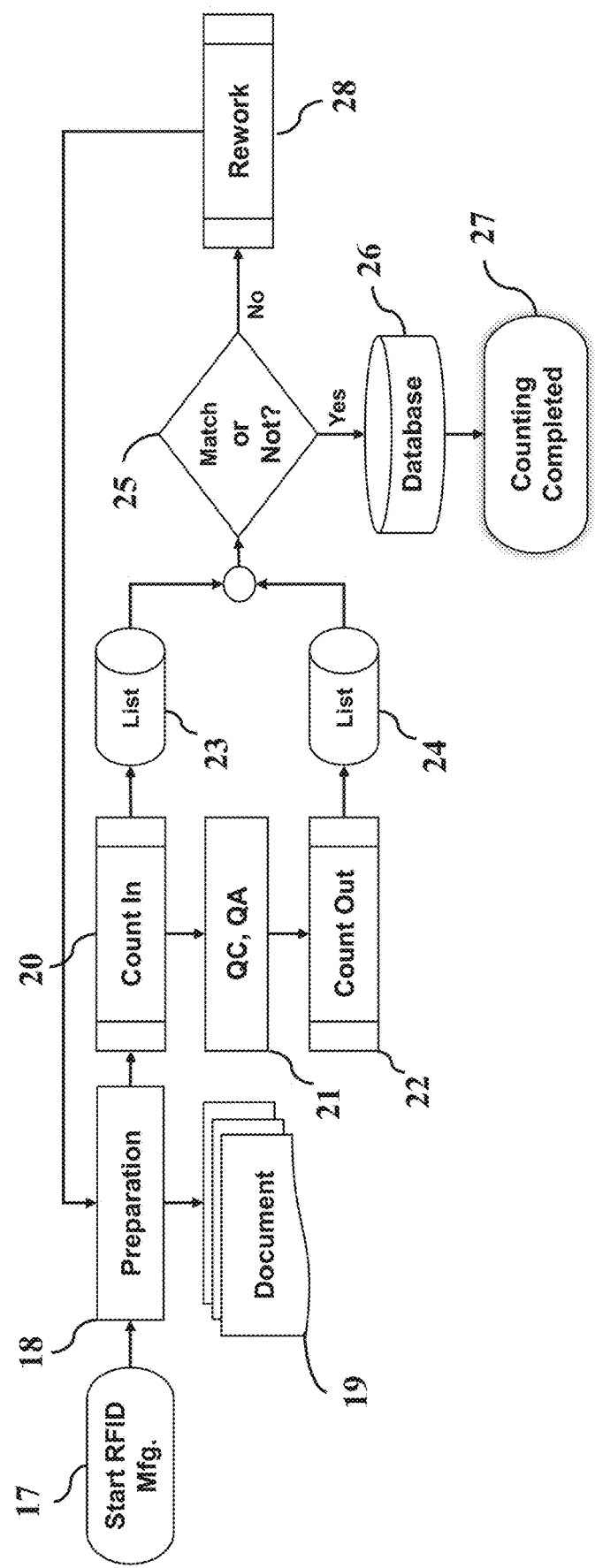
FIG. 7 is a detailed flowchart of the invention embodiment of using an UHF RFID scanner linked mobile device to show the complete method to enable count in and count out process for various articles at manufacturing production line to complete the whole counting process.

FIG. 7 is a detailed flowchart of the invention embodiment of using an UHF RFID scanner linked mobile device to show the complete method to enable count in and count out process for various articles at manufacturing production line to complete the whole counting process. When "Scan RFID" mode been selected and started 17, the invention of the scanning process when using an UHF RFID and method to enable count in and count out process for various sponges at manufacturing facilities, and to securely store counting record to database, such as product information, and unique identification for each sponge.

After preparation at production line 18 and associated manufacturing document 19, the batch of articles will be scanned by RFID reader as Count-in 20, then follow visual quality inspection 21 manually for perfection of each batch of articles. The present invention of specifically designed software on mobile device will general a list on user interface that could also show additional information about the article that information has been previously encoded into the UHF RFID chip accordingly. Then to perform count-out 22.

When required by users, information such as the type of the article, production batch or lot information, product name, SKU, descriptions, and/or pictures if needed for reference can be stored into the chip and to be shown by the specifically designed software for mobile devices by the present invention. The list 23 for count-in process and the list 24 for count-out process will be compared and checked 25. If both matched, all data generated by the counting process include count-in and count-out will be securely stored into the database 26 and 27. In the case of if the list for count-in and count-out of the same bundle of articles did not match, a predefined process for rework 28 will be conducted to ensure the quality of finished goods.

When "Scan RFID" mode been selected, FIGS. 8A-8F illustrate a flow of a process, respectively, of the invention of the scanning process when using an UHF RFID 16 and method to enable count in and count out process for various sponges at manufacturing facilities, and to securely store counting record to database, such as product information, and unique identification for each sponge.

The present invention of specifically designed software on mobile device could also show additional information about the article that information has been previously encoded into the UHF RFID chip as shown in FIGS. 8D and 8E. If required by users, information such as the type of the article, production batch or lot information, product name, SKU, descriptions, and/or pictures if needed for reference can be stored into the chip and to be shown by the specifically designed software for mobile devices by the present invention. All data generated by the counting process include count-in and count-out will be securely stored into the database as FIG. 8F.

3. Process of Counting and Identifying for Surgical Operations

The present invention provides a counting and tracking process using specifically designed UHF RFID for nurses to assist counting and identifying variety of objects that includes disposable and reusable medical devices or instrument during surgical operations, to ensure the accuracy of proper counting of multiple pieces of medical devises.

In additional to the traditional manual counting method and use of hanging sponge counter bag, the present invention of providing a counting and identifying process for the surgical sponges with UHF RFID tag attached are designated for using in medical or surgical operation procedures. The process tracking process is thereby able to provide a counting record to enhance the quality by reducing counting errors.

The RFID counting software provides quality record to be stored at database cloud indicating the presence of multiple medical devices with activated passive UHF RFID tag has been counted-in and counted-out during surgical procedures. This counting process helps confirm the manual count through the UHF RFID technology and locate a missing sponge outside the body that would be a significant improvement over most current practices in surgical operations.

The present invention comprises a process for facilitating counting of surgical sponges during the operations. This invention provides a process that includes RFID scanner and associated interface and software, to perform final varication of scanning all surgical sponges in the counter bags all at once and simultaneously, as a counted-out step. The software will identify each individual piece and to verify that every counted-out article after the operation matches every counted-in article before the operation.

In the case of a medical device missing after counted-out process, the RFID scanner with app may be used to assist finding the location or identifying of missing object with UHF RFID tag attached; additionally, assisting with visual and audio indicators.

The process for facilitating counting of surgical devices comprises: means for identifying and counting medical devices by an UHF RFID counting process, the counting process further having a recipe that identifies one or multiple pieces of medical devices before and after surgical operations; counting process with a database to identify UHF RFID tags that are physically associated with each of the medical devices when performing the scanned-in as counted-in and scanned-out as counted-out medical devices; and means to identify and verify the number of pieces scanned to match designated quantities, before and after surgical procedures, wherein the medical devices may be gauze sponges, lap sponges, or O.R. Towels.

The process of facilitating counting further comprised: select a search function in the application of user interface by using RFID scanner to find the missing medical device after counted-out process; use RFID scanner for locating missing object with UHF RFID tag attached, wherein visual and audio indicators are added to the user interface.

Figures 9A, 9B:
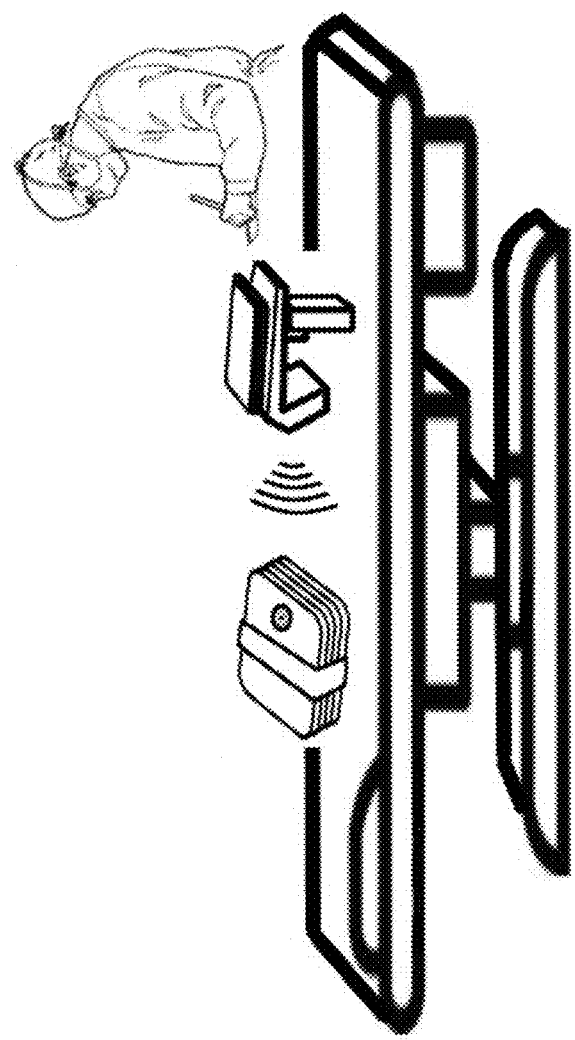
FIGS. 9A-9B illustrate an embodiment of the scanning process for using UHF RFID and for various sponges at surgical room in hospitals, to enable persons or groups of persons to login and access computer and network resources and devices such as PCs, workstations, laptops, mobile devices and the like, and to perform count-in and to securely store counting record to database.

FIGS. 9A-9B illustrate an embodiment of the scanning process for using UHF RFID and for various sponges at surgical room in hospitals, to enable persons or groups of persons to login and access computer and network resources and devices such as PCs, workstations, laptops, mobile devices and the like, and to perform count-in and to securely store counting record to database. An example of counting preparation before surgical operation. Associated team member will utilize a handheld RFID scanner with a linked mobile device to scan targeted articles with UHF RFID tags before the operation as FIG. 9A to perform counting process. Those articles with UHF RFID tags been prepared for the surgical operation will be scanned as count-in first. The user interface on the linked mobile device will show a list of those targeted unique articles been scanned, identified, and recorded. Surgical staff will perform surgical operation and utilized those uniquely counted and identified articles for the surgical operations.

Figures 10A, 10B, 10C:
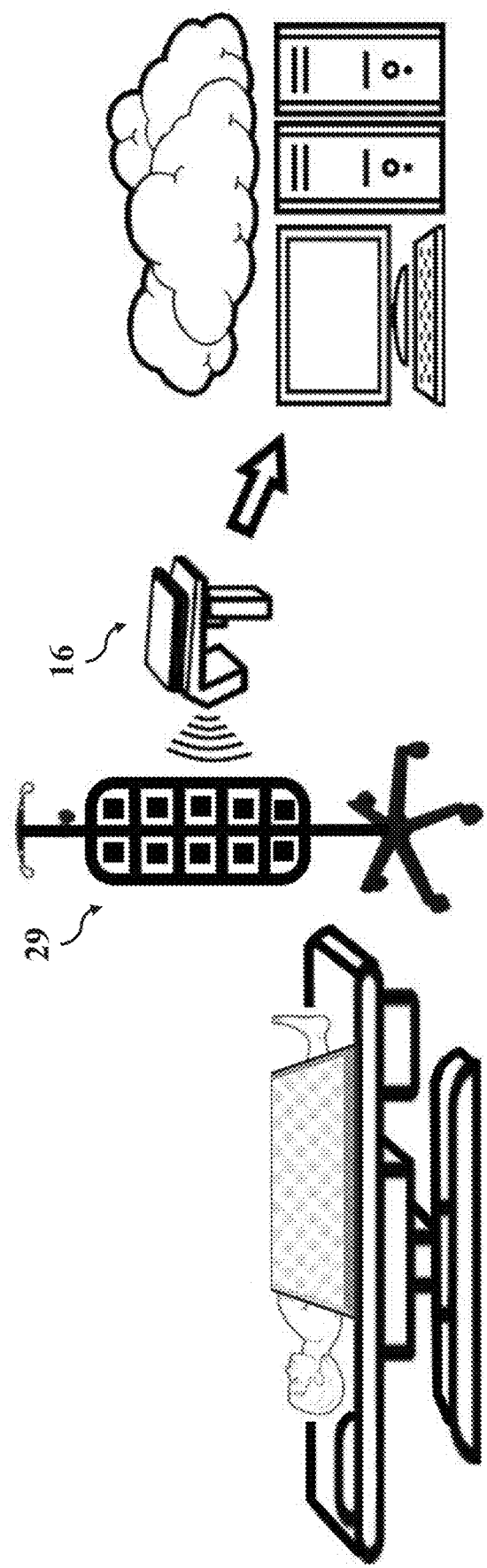
FIGS. 10A-10C illustrate an embodiment of the scanning process for using UHF RFID and for various articles in the counter bag after surgical operation at hospitals, this count-out process to be securely stored counting record to database.

FIGS. 10A-10C illustrate an embodiment of present invention of the scanning process for using UHF RFID and for various articles in the counter bag after surgical operation at hospitals, this count-out process to be securely stored counting record to database. Those counted-in articles been used during the surgical operation will be manually collected and put into counter bag 29 traditionally. While patient remains in the operation room FIG. 10A, as a general practice that articles been used may contain blood and other biological fluids to be collected and put into counter bag 29 as FIG. 10B, and then manually counted as count-out by surgical team member to confirm the number of the articles been used after the operation match to the number of article before the surgical operation when count-in.

Potential counting error may happen when using the traditional manual counting method occasionally, plus counting record is also lack of solid evidence that specific articles are recovered and identified after surgical operation. The present invention uses technologic assisted UHF RFID counting process, articles been placed into counter bag will be scanned by RFID scanner all together, during the surgical operation or preferably once the surgical operation has been completed FIG. 10B. All counted-in articles in counter bag 29 will be scanned by the RFID scanner 16 for the count-out process as FIG. 10B. All data generated by the counting process include count-in and count-out will be securely stored into the database as FIG. 10C accordingly.

The process of identifying and counting medical devices further comprising identifying and counting medical devices with UHF RFID tags before surgical operations to record the quantity using for the surgical operations first, respectively; after surgical operations, medical devices with UHF RFID tags to be scanned and counted-out, matching data from scanned-out to be correlated to initial scanned-in data, respectively; and verify and store counted-in and counted-out data to database or cloud as medical procedure record.

Figure 11:
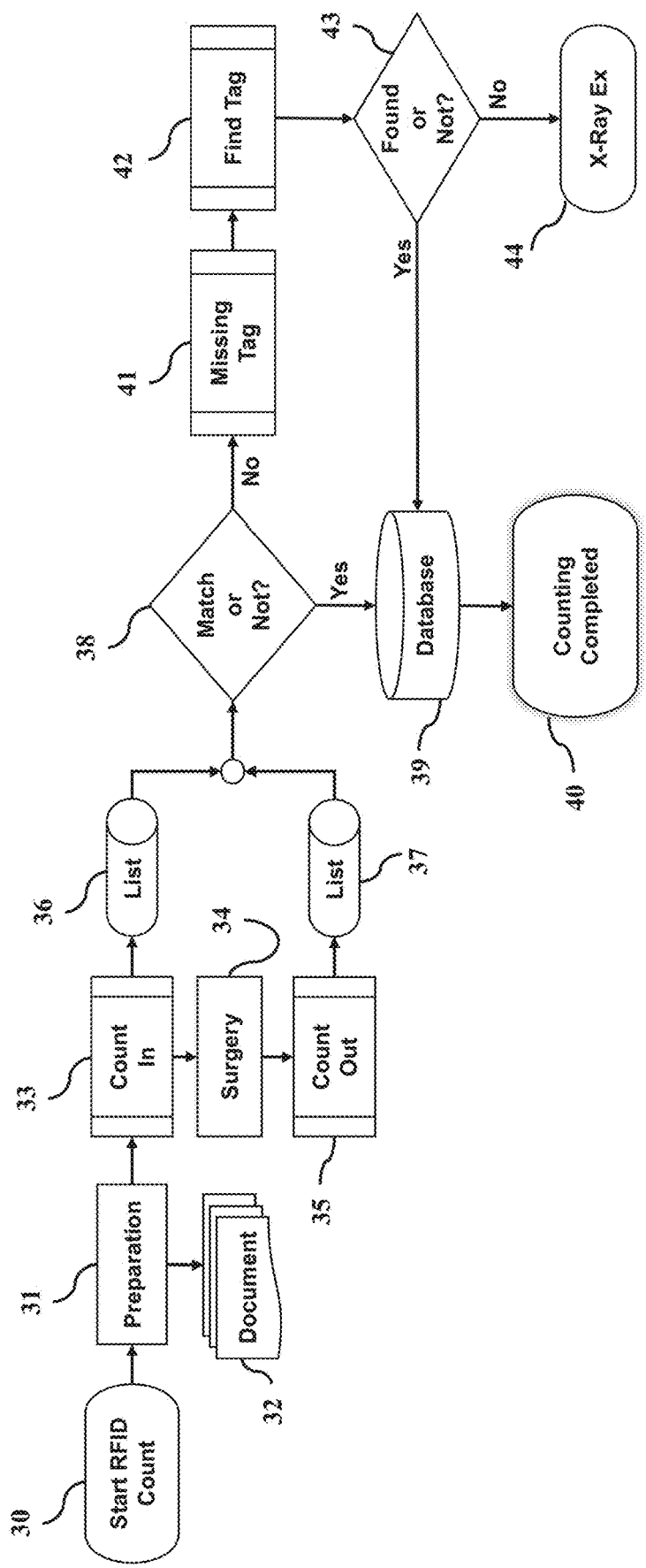
FIG. 11 is a detailed flowchart of the invention embodiment of using an UHF RFID scanner linked mobile device to show the complete method to enable count in and count out process for various articles at surgical room, to find missing UHF RFID pieces, and to complete the whole process.

FIG. 11 is a detailed flowchart of the invention embodiment of using an UHF RFID scanner linked mobile device to show the complete method to enable count in and count out process for various articles at surgical room, to find missing UHF RFID pieces, and to complete the whole process.

FIG. 11 illustrates a systematic flowchart of a key process when "Scan RFID" mode been selected 30 respectively, the present invention of the scanning process using an UHF RFID and method to enable count-in 33 and count-out 35 process for various articles at surgical room, and to securely store counting record to database, such as product information, and unique identification for each article. After the surgical operations 34, when all count-out articles match the unique identification of each count-in articles 38, a message of "completed" will be displayed to show the counting process for this operation has been completed successfully 40. All data generated by the counting process include a list of counted-in items 36 and a list counted-out items 37 will be securely stored into the database 39.

In an even that a missing article has been identified during the count-out process 41, because each article has unique identification of UHF RFID tag, missing article or miss-counted article can be searching for location by individually selecting the missing article to be searching at "Find Tag" mode 42. Passive UHF RFID tags wait for a signal from an RFID reader or scanner. The reader sends energy to an antenna which converts that energy into an RF wave that is sent into the read-zone. The missing article with UHF RFID tag is read within the read-zone, the RFID tag's internal antenna draws in energy from the RF waves and respond back to the RFID reader or scanner.

Once the missing article has been found 43, identified, and matched, the count-out process will be completed and shown on the user interface on mobile device. All data generated by the counting process include count-in and count-out will be securely stored into the database 39.

If a comprehensive searching in the surgical room has been performed, but surgical staff still unable to find the specific missing article 43, it would be necessary to call Radiology staff to provide further investigation by X-ray examinations 44.

Figure 12F:
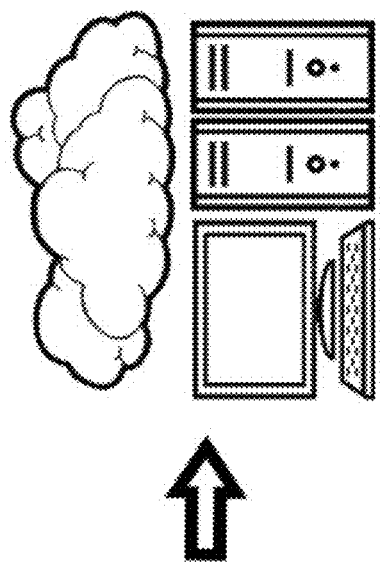
FIGS. 12A-12F illustrate a flow of a process, respectively, of the invention of the scanning process for using an UHF RFID and linked with a mobile device to show the complete method to enable count in and count out process for various sponges at surgical room in hospitals, and to securely store counting record to database or cloud.
Figure 12E:
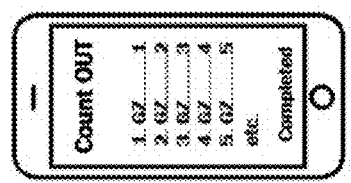
Figure 12D:
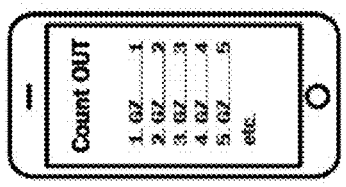
Figure 12C:
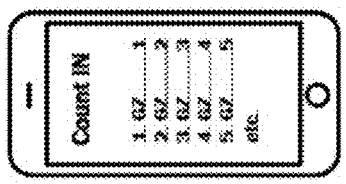
Figure 12B:
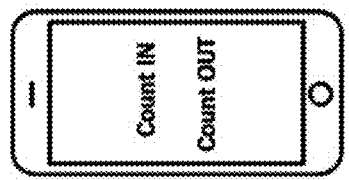
Figure 12A:
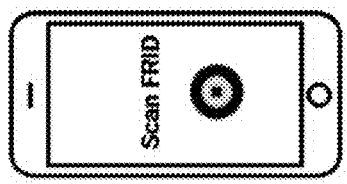

12A-12F illustrate a flow of a process, respectively, of the present invention of the scanning process for using an UHF RFID and linked with a mobile device to show the complete counting method to enable count-in FIG. 12C and count-out FIG. 12D process for various articles at surgical room in hospitals, and to securely store counting record to database. When "Scan RFID" mode been selected, FIG. 12A illustrates a flowchart of a process, respectively, of the invention of the scanning process when using an UHF RFID and method to enable count-in and count-out process FIG. 12B for various articles at surgical room, and to securely store counting record to database, such as product information, and unique identification for each sponge.

The present invention of specifically designed software on mobile device could also show additional information about the article that information has been previously encoded into the UHF RFID chip accordingly FIG. 12C to FIG. 12E. When all count-out articles match the unique identification of each count-in articles, a message of "completed" will be displayed to show the counting process for this operation has been completed successfully FIG. 12E. If required by users, additional information such as the type of the article, production batch or lot information, product name, SKU, descriptions, and/or pictures if needed for reference can be stored into the chip and to be shown by the specifically designed software for mobile devices by the present invention. All data generated by the counting process include count-in and count-out will be securely stored into the database as FIG. 12F.

Furthermore, the custom-build software for scanner linked with mobile device in present invention can block out all unintended or other untargeted RFID tags in complicated surgical environments, thus only focused on the specifically targeted surgical devices with unique custom-build UHF RFID tags. This will help simplify the counting process to count-in and count-out targeted surgical items only. Any other unwanted interference of RFID can be screened and blocked out that will not be shown on the user interface.

This invention provides counting process to accurately count and identify medical devices for healthcare providers to utilize a transparent, verifiable, standardized process to ensure "the counts are correct". Most importantly, those articles with unique identified UHF RFID tag have been previously verified at manufacturing facility with quality record been store at database, to be counted and verified again at surgical operation in hospitals with operation record been stored at database as well. Both sets of verified data present a solid quality record for supporting the present invention of counting process.

FIGS. 13A-13G show a more detailed of present invention of user interface for the mobile device of the invention embodiment of using an UHF RFID scanner linked mobile device to show the complete method to enable count in and count out process for various sponges at surgical room in hospitals, to find missing UHF RFID pieces, and to complete the whole process. In an even that a missing article has been identified during the count-out process FIG. 13B, because each article has unique identification of UHF RFID tag, missing article or miss-counted article will be highlighted FIG. 13C.

Figure 13G:
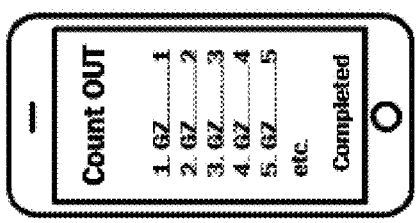
FIGS. 13A-13G show a more detailed interface of the mobile device of the invention embodiment of using an UHF RFID scanner linked mobile device to show the complete method to enable count in and count out process for various articles at surgical room in hospitals, to find missing UHF RFID pieces, and to complete the whole process.
Figure 13F:
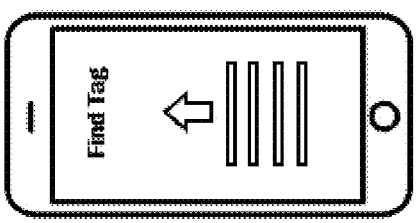
Figure 13E:
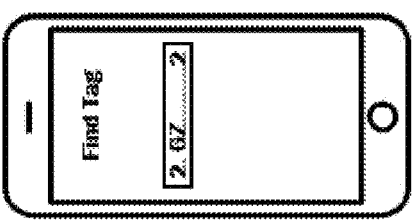
Figure 13D:
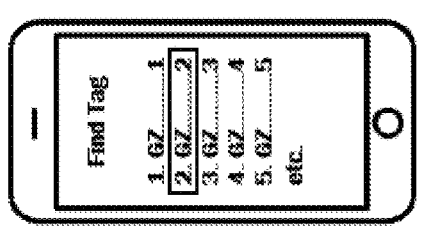
Figure 13C:
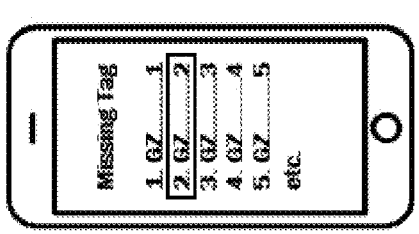
Figure 13B:
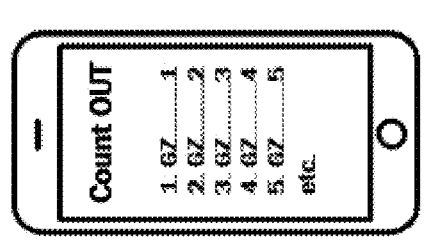
Figure 13A:
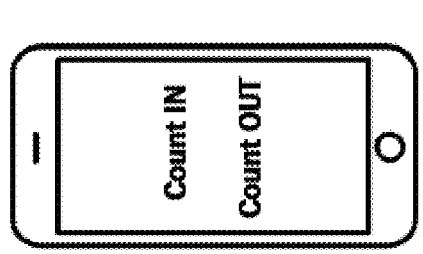

Select the specific missing article from the list of counted-out to be searching at "Find Tag" mode FIG. 13D, wherein the missing article will be selected and highlighted FIG. 13E. Since the UHF RFID tag been utilized for this invention are passive tag and wait for a signal from an RFID reader or scanner, the reader sends energy to an antenna which converts that energy into an RF wave that is sent into the read-zone.

Use the UHF RFID scanner to sweep surgical operation area for searching and finding the missing medical device with a targeted UHF RFID tag. Once the missing article with UHF RFID tag is read within the read-zone, the UHF RFID tag's internal antenna draws in energy from the RF waves and respond back to the RFID reader or scanner. The specifically designed and customized program for this invention provides a responsive, audible, signal-strength, and a dynamic graphical signal to be shown FIG. 13F, wherein the missing UHF RFID tag is specifically locked with the targeted article to be searching for.

Check the intensity of the audio and graphic signal to be increased when the missing article with specific identification has been scanned, detected, checked and identified. When the scanner is getting closer to the missing article in the read-zone, the higher the intensity to be shown FIG. 13F. Once the missing article has been found, identified, and matched, the count-out process will be completed and shown on the user interface of mobile device FIG. 13G. The counting process for targeted surgical operation is completed.

4. Process of Counting and Identifying by Using Two-Dimensional Data Matrix Barcodes for Manufacturing Process and Surgical Operations For the purpose of counting surgical sponges, customized information will be pre-printed on each 2DDM barcode label to provide unique identification for each label that will be attached to the surface of each surgical device. By using 2DDM barcode scanner, each device with unique 2DDM tag can be scanned as count-in and count-out process as a counting process for manufacturing process and surgical operations. The present invention demonstrated that an embodiment of using the same scanner linked mobile device for scanning 2DDM to show the complete method to enable count-in and count-out process for various surgical devices. Alternatively, the same handheld scanner also has the function for scanning liner barcode or two-dimensional data matrix tags by selecting desired function for scanning either RFID or 2D data matrix.

FIGS. 14A-14F illustrate an embodiment of using the same scanner linked mobile device for scanning 2DDM to show the complete method to enable count in and count out process for various sponges. Alternatively, the same handheld scanner also has the function for scanning liner barcode or two-dimensional data matrix tags by selecting desired function for scanning either RFID or data matrix. FIG. 14A illustrates an embodiment of using the same handheld scanner with linked mobile device for scanning articles having 2DDM tag as 45 to show another complete method as an option to enable count-in and count-out process for various articles with 2DDM tag attached.

Depends upon the type of articles been selected for using this technologic assisted counting process, two different options can be selected individually for its associated counting process. The present invention included a specifically designed software for the linked mobile device that can be utilized for UHF RFID application or 2DDM application as FIG. 14A.

Once "Scan 2DDM" option has been selected on FIG. 14B, the user interface software on linked mobile devise will show a selection for the counting process as FIG. 14C. The counting method will start by selecting count-in first at user interface in FIG. 14C. A activated scanner with linked mobile device will start count-in process manually by click the 2DDM option and let scanner facing the 2DDM tag of targeted articles with unique identification of 2DDM tags.

After the 2DDM tag has been scanned, the user interface on mobile device will show a list of targeted articles that been scanned, detected, and counted-in as FIG. 14D. An example of bundle of five pieces surgical sponges been counted-in, a list of unique identified article to show those 5 surgical sponges as FIG. 14D. The same scanning process will be performed for count-out.

Once all counted-in articles have been scanned, identified, and recorded by scanner, the user interface will show the counting process has been completed FIG. 14E. All data generated by the counting process include count-in and count-out will be securely stored into the database as FIG. 14F.

The present invention provides accurately counted and absolutely correct quantities of medical devices as requested to healthcare users would be one the most important tasks for manufactures as great starting point for defending challenges from potential counting issues. Utilizing UHF RFID technologies to tag with medical devices not only provides an accurate counting method, but also provides quality document of manufacturing production record and also reliable counting record for surgical procedure as solid evidence of a quality record for traceability.

The invention claimed is:

1. A UHF RFID tag system comprising:
   a set of disposable medical devices;
   a set of UHF RFID tags mounted to the set of disposable medical devices;
   a UHF RFID tag in the set of UHF RFID tags having a microchip, wherein the UHF RFID tag comprises:
   an integrated circuit, wherein the integrated circuit is electrically connected to the microchip, wherein the microchip has a memory, wherein the memory stores an identification number and a device description;
   an antenna made of electrically conducting material, wherein the antenna is electrically connected to the integrated circuit;

a substrate, wherein the substrate supports the antenna, integrated circuit and microchip;
an overlay made of RF translucent material that provides a laminate water resistant or waterproof covering for the antenna, integrated circuit and microchip; and
a UHF RFID scanner, wherein the antenna receives radio signals and transmits radio signals to the UHF RFID scanner, wherein the antenna converts the radio signals into radio wave power;
a database retaining the identification number, wherein the UHF RFID scanner is a mobile device and configured to count in and count out the set of UHF RFID tags, wherein the set of UHF RFID tags are scannable with the UHF RFID scanner or an optical scanner of the UHF RFID scanner, wherein the UHF RFID scanner is configured to give a match indication when UHF RFID tags counted-out matches UHF RFID tags counted-in, wherein the set of disposable medical devices includes at least one surgical sponge, wherein the at least one surgical sponge has a 2DDM barcode in addition to the UHF RFID tag, wherein the identification number further includes material specifications, wherein the UHF RFID scanner is configured with a non match indication that identifies and highlights a missing UHF RFID tag on a UHF RFID tag list and provides a search function to find the missing UHF RFID tag, wherein the UHF RFID scanner has an audio indicator to assist a user search, wherein the audio indicator is higher intensity when the UHF RFID scanner is closer to the missing UHF RFID tag, wherein the UHF RFID scanner has a graphical indicator to assist a user search, wherein the graphical indicator is higher intensity when the UHF RFID scanner is closer to the missing UHF RFID tag, wherein the UHF RFID scanner is configured to connect to a linked mobile device and display the UHF RFID tag list on the linked mobile device, wherein the overlay is PVC or PE, wherein X-ray detectable material is added to the substrate, wherein the includes barium sulfate, wherein the UHF RFID tag is heat pressed to a medical device in the set of disposable medical devices with a polyurethane based resin heat sensitive adhesive, wherein the UHF RFID tag is heat pressed to a sponge or towel with an adhesive resin at between 200° F. to 350° F. with pressure of 50 pounds per square inch to 100 pounds per square edge for less than 10 seconds, wherein the UHF RFID tag has an optically scannable identifier, wherein the UHF RFID scanner is also an optical scanner that is configured to scan the optically scannable identifier, wherein the database further includes a scanned set of disposable medical devices entered by scanning each item in the set of disposable medical devices using an RFID shielding cage for isolating the signals of each item in the set of disposable medical devices, wherein the set of disposable medical devices includes a bundle of surgical gauzes, wherein each surgical gauze in the bundle of surgical gauzes has a unique UHF RFID tag selected from the set of UHF RFID tags, wherein the bundle of surgical gauzes is bundled together with a paper band having adhesive at one end, wherein the RFID shielding cage includes a copper mesh door with conductive gaskets, wherein the UHF RFID tag has an optically scannable identifier that is scanned to the database during manufacturing in addition to the UHF RFID scanning of the UHF RFID tag; further including a display with a user interface on the mobile device, wherein the user interface provides a selection for a counting process, wherein the user interface displays a list of targeted articles of the set of disposable medical devices that have been scanned, detected and counted in, wherein the mobile device further includes a "Scan RFID" mode for UHF RFID scanning, wherein the mobile device is configured to verify scanning of all surgical sponges in the set of medical devices in counter bags all at once and simultaneously; wherein the mobile device is configured to show a message of "completed" when the counting process is completed successfully, whereby UHF RFID tag system provides accurately counting of surgical devices for healthcare users in one mobile device and maintains a record for surgical devices used in surgical procedures.

* * * * *